US012616423B2

(12) United States Patent
Jang

(10) Patent No.: US 12,616,423 B2
(45) Date of Patent: May 5, 2026

(54) APPARATUS AND METHOD FOR ESTIMATING PHYSIOLOGICAL VARIABLES

(71) Applicant: SAMSUNG ELECTRONICS CO., LTD., Suwon-si (KR)

(72) Inventor: Dae Geun Jang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 381 days.

(21) Appl. No.: 18/121,453

(22) Filed: Mar. 14, 2023

(65) Prior Publication Data

US 2024/0115212 A1 Apr. 11, 2024

(30) Foreign Application Priority Data

Oct. 7, 2022 (KR) ........................ 10-2022-0128917

(51) Int. Cl.
*A61B 5/00* (2006.01)

(52) U.S. Cl.
CPC ............ *A61B 5/7278* (2013.01); *A61B 5/681* (2013.01); *A61B 5/746* (2013.01); *A61B 2560/0223* (2013.01)

(58) Field of Classification Search
None
See application file for complete search history.

(56) References Cited

U.S. PATENT DOCUMENTS 11,266,375 B2    3/2022 Wohlschlager et al.
11,382,598 B2    7/2022 Wohlschlager et al.

| | | |
|---|---|---|
| 2016/0361029 A1 | 12/2016 | Kang et al. |
| 2020/0054223 A1 | 2/2020 | Kwon et al. |
| 2020/0085324 A1 | 3/2020 | Moser et al. |
| 2021/0076960 A1 | 3/2021 | Fornwalt et al. |
| 2021/0177287 A1* | 6/2021 | Kwon ................ A61B 5/02233 |
| 2023/0091997 A1 | 3/2023 | Cho |

FOREIGN PATENT DOCUMENTS

| | | |
|---|---|---|
| JP | 2018-527101 A | 9/2018 |
| KR | 10-2016-0146393 A | 12/2016 |
| KR | 10-2020-0021207 A | 2/2020 |
| KR | 10-2020-0045445 A | 5/2020 |
| KR | 10-2021-0066322 A | 6/2021 |
| KR | 10-2021-0147379 A | 12/2021 |

(Continued)

OTHER PUBLICATIONS

Office Action dated Sep. 18, 2024, issued by Korean Patent Office in Korean Patent Application No. 10-2022-0128917.

(Continued)

*Primary Examiner* — George R Evanisko
(74) *Attorney, Agent, or Firm* — Sughrue Mion, PLLC

(57) ABSTRACT

An apparatus for estimating physiological variables includes: a sensor configured to measure a bio-signal from an object; and a processor. The processor is configured to: configure input data for use in a neural network-based physiological variable estimation model based on bio-signal data measured at different times by the sensor, and input the configured input data to the physiological variable estimation model to obtain a variation in physiological variables over a time period from a calibration time to a current time.

3 Claims, 13 Drawing Sheets

(56)           References Cited

FOREIGN PATENT DOCUMENTS

| | | | |
|---|---|---|---|
| KR | 10-2022-0008601 | A | 1/2022 |
| KR | 10-2359362 | B1 | 2/2022 |
| KR | 10-2022-0095009 | A | 7/2022 |
| KR | 10-2022-0105092 | A | 7/2022 |

OTHER PUBLICATIONS

Communication issued May 24, 2025 by the Korean Intellectual Property Office in Korean Patent Application No. 10-2022-0128917.

Madhuri Panwar et al., "PP-Net: A Deep Learning Framework for PPG-Based Blood Pressure and Heart Rate Estimation", 2020, IEEE Sensors Journal, vol. 20, No. 17, 12 pages total.

Slapniar et al., "Blood Pressure Estimation from Photoplethysmogram Using a Spectro-Temporal Deep Neural Network", 2019, Sensors, vol. 19, 17 pages total.

Schlesinger et al., "Blood Pressure Estimation from PPG Signals Using Convolutional Neural Networks and Siamese Network", 2020, IEEE ICASSP, 5 pages total.

* cited by examiner

APPARATUS AND METHOD FOR ESTIMATING PHYSIOLOGICAL VARIABLES

CROSS-REFERENCE TO RELATED APPLICATION(S)

This application claims priority from Korean Patent Application No. 10-2022-0128917, filed on Oct. 7, 2022, in the Korean Intellectual Property Office, the entire disclosure of which is incorporated herein by reference for all purposes.

BACKGROUND

1. Field

The following description relates to technology for configuring input data for a physiological variable estimation model based on bio-signals measured non-invasively, and for estimating physiological variables by using the input data.

2. Description of Related Art

Research on information technology (IT)—medical convergence technology, in which IT and medical technology are combined, is being recently carried out to address medical challenges such as the aging population structure, rapid increase in medical expenses, and shortage of specialized medical service personnel. Monitoring of the health condition of the human body may not be limited to a fixed place, such as a hospital, but may expand to include a mobile healthcare sector for monitoring a user's health condition at any time and any place in daily life at home and office. Electrocardiography (ECG), photoplethysmogram (PPG), and electromyography (EMG) signals are examples of bio-signals that may indicate an individual's health condition. A variety of signal sensors are being developed to measure such signals in daily life. Particularly, by using a PPG sensor, it is possible to estimate blood pressure of the human body by analyzing the shape of pulse wave that reflects cardiovascular status.

SUMMARY

An apparatus for estimating physiological variables may include: a sensor configured to measure a bio-signal from an object; and a processor. The processor may be configured to: configure input data for use in a neural network-based physiological variable estimation model based on bio-signal data measured at different times by the sensor, and input the configured input data to the physiological variable estimation model to obtain a variation in physiological variables over a time period from a calibration time to a current time.

The apparatus may further include a memory configured to store the bio-signal data corresponding to the calibration time. When the sensor measures a bio-signal at the current time for estimating the physiological variables, the processor may be configured to collect the bio-signal data corresponding to the calibration time from the memory.

The bio-signal may include at least one of photoplethysmogram (PPG), Electrocardiography (ECG), Electromyography (EMG), impedance plethysmogram (IPG), Pressure wave, video plethysmogram (VPG), Speckle-plethysmogram (SPG), Magnetic-plethysmograph (MPG), Ballistocardiogram (BCG), or Seismocardiogram (SCG).

The bio-signal data may include at least one of: raw data of the bio-signal measured by the sensor, preprocessed data obtained by preprocessing the raw data, representative waveform data extracted from the raw data or the preprocessed data, multi-dimensional data converted from the raw data or the preprocessed data, or feature data extracted from the raw data or the preprocessed data, the feature data being associated with the physiological variables.

The processor being configured to configure input data may include being configured to use the bio-signal data to configure the input data as multi-channel input data to be input to an input layer of the neural network-based physiological variable estimation model.

In response to the bio-signal data differing in length, the processor may be configured to adjust each of the bio-signal data to be equal in length by normalizing the bio-signal data by (i) adding a predetermined padding value to each of the bio-signal data having a shorter length in comparison to a predetermined length, and (ii) cutting a predetermined region of bio-signal data having a longer length in comparison to the predetermined length.

The processor being configured to configure the input data may include being configured to: extract a feature associated with the physiological variables from the measured bio-signal, normalize the extracted feature associated with the physiological variables based on a calibration feature at the calibration time, and configure the input data based further on the normalized value.

The processor being configured to configure the input data may be based further on at least one of a physiological variable value at the calibration time or user information.

The variation in physiological variables may include at least one of a difference and a ratio between the physiological variable value at the calibration time or a physiological variable value at a current time.

Based on the obtained variation in physiological variables, the processor may be configured to estimate the physiological variables including at least one of blood pressure, blood glucose, body temperature, antioxidant level, or triglyceride level.

The processor may be configured to estimate the physiological variables by combining the obtained variation in physiological variables and the physiological variable value at the calibration time.

A method of estimating physiological variables may include: collecting, by a processor, bio-signal data measured at different times by a sensor; configuring input data for a neural network-based physiological variable estimation model based on the collected bio-signal data at different times; and inputting the configured input data to the physiological variable estimation model to obtain a variation in physiological variables over a time period from a calibration time to a current time.

The collecting the bio-signal data may include receiving a bio-signal measured at the current time by the sensor and collecting one or more bio-signal data corresponding to the calibration time from a memory.

The configuring the input data may include using the bio-signal data to configure the input data as multi-channel input data to be input to an input layer of the neural network-based physiological variable estimation model.

The configuring the input data may include, in response to the bio-signal data differing in length, adjusting each of the bio-signal data to be equal in length by normalizing the bio-signal data by (i) adding a predetermined padding value to bio-signal data having a shorter length in comparison to a predetermined length, and (ii) cutting a predetermined region of bio-signal data having a longer length in comparison to the predetermined length.

The configuring the input data may be based further on a value obtained by normalizing a feature associated with physiological variables at the current time based on a calibration feature at the calibration time.

The configuring the input data may be based further on at least one of a physiological variable value at the calibration time or user information.

The variation in physiological variables may include at least one of a difference and a ratio between the physiological variable value at the calibration time or a physiological variable value at the current time.

The method may further include estimating the physiological variables by combining the obtained variation in physiological variables and the physiological variable value at the calibration time.

An apparatus for estimating physiological variables may include: a sensor configured to measure a bio-signal from an object; and a processor. The processor may be configured to: configure input data for use in a neural network-based physiological variable estimation model based on bio-signal data measured at different times from the object by the sensor, and input the configured input data and a physiological variable value at a calibration time to the physiological variable estimation model to obtain a physiological variable value a current time.

The sensor may be wearable by the object on at least one of a wrist and head of the object.

The object may be a body part of a user. The user information may include at least one of age, gender, weight, or height of the user.

The processor may be further configured to: receive a physiological variable estimation result from the physiological variable estimation model, and generate a warning or an action based on the received physiological variable estimation result.

Figure 1:
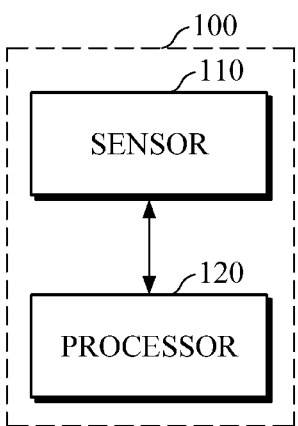
FIG. 1 is a block diagram illustrating an apparatus for estimating physiological variables according to an embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of other embodiments are included in the following detailed description and drawings. Advantages and features of example embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

FIG. 1 is a block diagram illustrating an apparatus for estimating physiological variables according to an embodiment of the present disclosure. FIGS. 2A to 2E are diagrams explaining examples of configuring input data for a physiological variable estimation model and estimating physiological variables.

The apparatus for estimating physiological variables may be implemented as an electronic device, such as a smartphone, a tablet PC, a desktop computer, a laptop computer, or an wearable device, such as a wristwatch wearable device, a bracelet wearable device, a wristband wearable device, a ring wearable device, a glasses wearable device, and a headband wearable device. The wearable device may include, for example, a strap or other attachment mechanism configured to maintain contact between the sensor and the object.

Referring to FIG. 1, an apparatus 100 for estimating physiological variables includes a sensor 110 and a processor 120.

The sensor 110 may measure a bio-signal from an object. For example, the bio-signal may include Photoplethysmogram (PPG), Electrocardiography (ECG), Electromyography (EMG), impedance plethysmogram (IPG), Pressure wave, video plethysmogram (VPG), Speckle-plethysmogram (SPG), Magnetic-plethysmograph (MPG), Ballistocardiogram (BCG), and Seismocardiogram (SCG). In this case, the object may be a body part making contact with or adjacent to the sensor 110, and may be a body part where pulse waves may be easily measured. For example, the object may be the skin of the wrist that is adjacent to the radial artery and an upper part of the wrist where venous blood or capillary blood passes. However, the object, as used in this disclosure, is not limited thereto, and may be, for example, a peripheral part of the body, such as a finger, or a toe, which is a region with high blood vessel density.

For example, the sensor 110 may include a PPG sensor for measuring a PPG signal from an object. The PPG sensor may include one or more light sources for emitting light to an object and one or more detectors for detecting light scattered or reflected from or transmitted into the object after light is emitted by the light source to the object. In this case, the light source may include a light emitting diode (LED), a laser diode (LD), and a phosphor. The light source may emit light of one or more wavelengths (e.g., green, red, blue, and infrared wavelengths). In addition, the detector may include sensors such as one or more photodiodes, photo transistors (PTr), and/or image sensors (e.g., complementary metal-oxide semiconductor (CMOS) image sensor), but is not limited thereto.

The processor 120 may be electrically or functionally connected to the sensor 110 and may control the sensor 110 to measure a bio-signal from an object for calibration or for estimation of physiological variables.

The processor 120 may estimate physiological variables by using bio-signal data, measured at different times by the sensor 110, and a physiological variable estimation model. The physiological variable estimation model may be, for example, Neural Network (NN), Deep Neural Network (DNN), Convolutional Neural Network (CNN), or Recurrent Neural Network (RNN), but is not limited thereto, and may be various types of neural network-based models and may be pretrained by machine learning such as deep learning. The physiological variable estimation model may be trained to output a variation in physiological variables between a previous calibration time and a current time at which physiological variables are to be estimated, or may be trained to output a physiological variable value at the current time.

In this case, the physiological variable may be blood pressure, but is not limited thereto and may include, for example, blood pressure, blood glucose, body temperature, antioxidant level, and triglyceride level. For convenience of explanation, the following description will be given using blood pressure as an example.

For example, once the sensor 110 measures a bio-signal for estimating blood pressure, the processor 120 may collect bio-signal data at the current time by receiving the bio-signal measured by the sensor 110 and may collect bio-signal data, measured at least one or more times at the previous calibration time, from a memory, cloud, and/or another electronic device. In this case, the bio-signal data may be in the form of raw data of the bio-signal itself measured by the sensor 110. Alternatively, the bio-signal data may be data obtained by preprocessing the raw data, representative waveform data extracted from the raw data or the preprocessed data, feature data associated with blood pressure and extracted from the raw data or the preprocessed data, multidimensional data (e.g., spectrogram) obtained by converting the raw data or the preprocessed data.

For example, the processor 120 may obtain the preprocessed data by performing preprocessing, such as filtering of the raw data (e.g., band-pass filtering between 0.4 Hz and 10 Hz), amplification of the bio-signal, converting the signal into a digital signal, smoothing, ensemble averaging of continuously measured bio-signals. In addition, the processor 120 may extract a predetermined time interval or a signal during one cycle as a representative waveform from the raw data or the preprocessed data, or may extract a representative waveform by overlapping a plurality of time intervals or a plurality of periodic signals. Alternatively, the processor 120 may convert the raw data or the preprocessed data into a multi-dimensional signal such as spectrogram. Alternatively, the processor 120 may extract a feature associated with blood pressure from the raw data or the preprocessed data.

Generally, it is known that a variation in mean arterial pressure (MAP) is proportional to cardiac output (CO) and total peripheral resistance (TPR). Accordingly, the processor 120 may extract features associated with CO and/or TPR. Here, the feature associated with CO (hereinafter referred to as a CO feature) may be a feature value which shows an increasing/decreasing trend in proportion to an actual CO value when the actual CO value relatively increases/decreases compared to resting cardiac output. Further, the feature associated with TPR (hereinafter referred to as a TPR feature) may be a feature value which shows an increasing/decreasing trend in proportion to an actual TPR value when the actual TPR value relatively increases/decreases compared to resting total peripheral resistance.

Accordingly, the processor 120 may extract the CO feature and/or the TPR feature by using the raw data or the preprocessed data, and/or a second derivative signal of the raw data or the preprocessed data. For example, the processor 120 may extract heart rate (HR), time values of the respective waveform components and amplitude values corresponding to the time values in the second derivative signal of the raw data or the preprocessed data, a time value and an amplitude value of a point at which an amplitude has a maximum value in a systolic region of the raw data or the preprocessed data, a time value and an amplitude value of a point at which a slope is closest to zero in the systolic region of the raw data or the preprocessed data, a time value and an amplitude value of an internally dividing point between time values of adjacent waveform components in the second derivative signal, one or an appropriate combination of two or more of a total or partial area of the raw data or the preprocessed data, duration, cycle, and pulse pressure as features associated with blood pressure from the second derivative signal. However, the features are not limited thereto.

The processor 120 may configure input data for a blood pressure estimation model by using the collected bio-signal data at different times. In this case, the processor 120 may configure the input data by using one type of bio-signal data among various types of data described above, or by combining two or more different types of bio-signal data. For example, the processor 120 may configure the bio-signal data as multi-channel input data to correspond to an input layer of a blood pressure estimation model. In this case, if the collected bio-signal data differ in length, the processor 120 may adjust the data to be equal in length.

For example, the processor 120 may add a predetermined padding value to bio-signal data having a short length compared to a predetermined length. For example, by using, as the padding value, an amplitude value in a predetermined interval (e.g. time interval of 0 to 1) of the bio-signal data having a short length, a statistical value, such as a mean value, a minimum value, a maximum value, etc., of all amplitude values, an arbitrary fixed value, etc., the processor 120 may add the padding value at the end of the bio-signal data. In this case, the predetermined length may be defined as, for example, a length of a bio-signal at a calibration time or a length of a bio-signal at a current time. However, the predetermined length is not limited thereto, and may be defined as, for example, an arbitrary fixed constant value based on the number of samples to be input to each node of an input layer of a blood pressure estimation model.

In another example, the processor 120 may cut a predetermined region of bio-signal data having a longer length compared to the predetermined length, or may normalize the bio-signal data. For example, the processor 120 may cut a leading portion or a trailing portion of the entire bio-signal data. Alternatively, the processor 120 may extract values at predetermined time intervals from the bio-signal data according to the predetermined length, and may normalize the extracted values by connecting the values. The processor 120 may obtain a variation in blood pressure between a calibration time and a current time by inputting the configured input data to a blood pressure estimation model. The blood pressure estimation model may perform sampling by extracting a predetermined number of samples from each channel data of the input data, and may input values, obtained by samplings, to an input node of the input layer and may output a blood pressure variation ΔBP through an output node. In this case, the output node may include an output node for outputting an SBP variation ΔSBP and an output node for outputting a DBP variation ΔDBP, and the respective output nodes may output the SBP variation ΔSBP and the DBP variation ΔDBP, respectively. In this case, the blood pressure variation ΔBP may be defined as, for example, a difference Ymeas−Ycal between a blood pressure value (e.g., Ycal) at the calibration time and a blood pressure value (Ymeas) at a blood pressure estimation time, or a ratio (Ymeas/Ycal) between the blood pressure values.

In addition, once the blood pressure estimation model outputs the blood pressure variation, the processor 120 may obtain a blood pressure value at a blood pressure estimation time by linearly combining the blood pressure variation and a calibration blood pressure value as shown in the following Equation 1. In this case, a reference blood pressure value may be a blood pressure value measured at the calibration time by using, for example, a cuff sphygmomanometer.

$$BP_{est}=\Delta BP_{est}+BP_{cal} \qquad \text{[Equation 1]}$$

Herein, $\Delta BP_{est}$ denotes the blood pressure variation at the blood pressure estimation time, $BP_{est}$ denotes a final blood pressure value, and $BP_{cal}$ denotes a calibration blood pressure value at the calibration time.

In one embodiment, the processor 120 may further collect additional data in addition to bio-signal data, and by using the collected additional data along with the bio-signal data, the processor 120 may configure the input data for the blood pressure estimation model. In this case, the additional data may include, for example, a blood pressure value at the calibration time, user information (e.g., age, gender, weight, height, etc.), and/or feature data associated with blood pressure.

For example, the processor 120 may collect the blood pressure value at the calibration time and/or user information from a memory, cloud, another electronic device, and/or user input. In addition, the processor 120 may extract the feature associated with blood pressure from the raw data or preprocessed data at the current time as described above, and may normalize the extracted feature based on the feature associated with blood pressure at the calibration time and may add the normalized value to the input data. For example, the processor 120 may normalize the feature by subtracting a feature value at the calibration time from a feature value at the current time and by dividing a resultant value by the feature value at the calibration time. However, the normalization is not limited thereto.

Figure 2A:
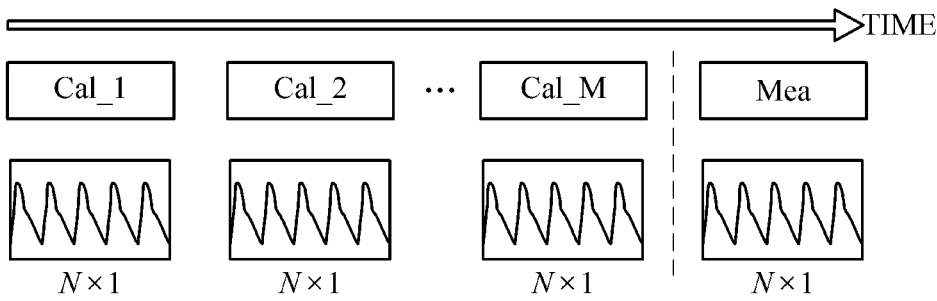
FIGS. 2A to 2E are diagrams explaining examples of configuring input data for a physiological variable estimation model and estimating physiological variables.
Figure 2B:
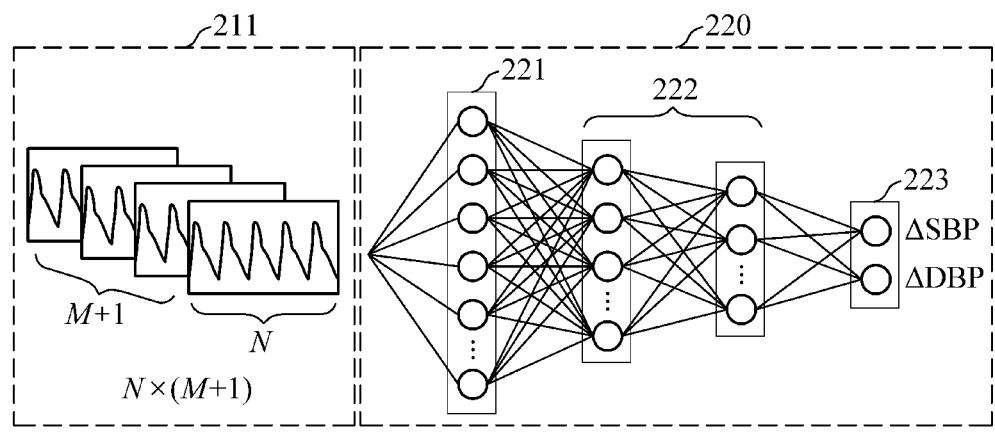

FIG. 2A is a diagram illustrating an example of obtaining, as bio-signal data, M number of raw data Cal_1, Cal_2, . . . , and Cal_M having a time length N at a calibration time and raw data Mea at a blood pressure estimation time. In this case, the M number of raw data Cal_1, Cal_2, . . . , and Cal_M at the calibration time may be bio-signals measured M number of times at predetermined time intervals (e.g., two minutes). FIG. 2B is a diagram illustrating an example of obtaining blood pressure variations ΔSBP and ΔDBP by configuring an input data 211 in the form of multi-channel input data N×(M+1) based on (M+1) number of bio-signal data having the time length N, and by inputting the input data 211 to a blood pressure estimation model 220. Here, it is assumed that the bio-signal data have the same time length N, but if the bio-signal data differ in time length, the processor 120 may adjust the bio-signal data to be equal in time length.

Figure 2C:
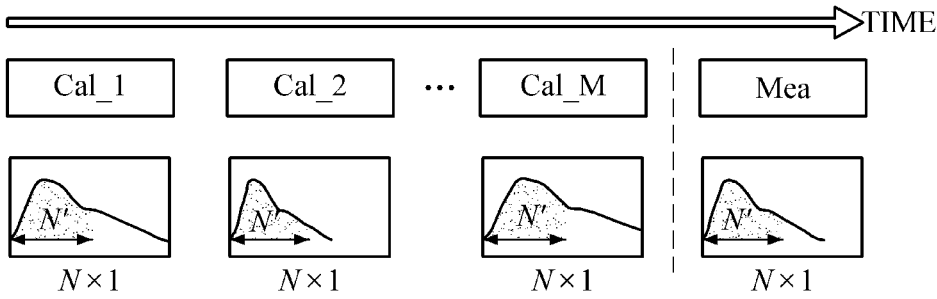
Figure 2D:
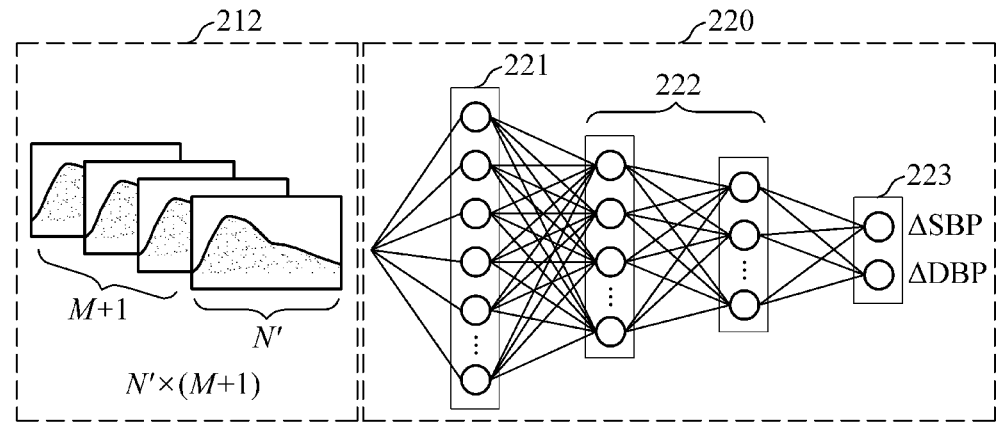

FIG. 2C is a diagram illustrating an example of obtaining bio-signal data by extracting representative waveforms having a time length N' from each of (M+1) number of raw data having the time length N. FIG. 2D is a diagram illustrating an example of obtaining blood pressure variations ΔSBP and ΔDBP by configuring input data 212 in the form of N'×(M+1) based on (M+1) number of representative waveforms having the time length N', and by inputting the input data 212 to the blood pressure estimation model 220.

The blood pressure estimation model 220 in FIGS. 2B and 2D is an example of a simple neural network-based model and may include an input layer 221, one or more hidden layers 222, and an output layer 223. However, the model is not limited thereto, and the type of neural network model, the number of hidden layers 222, and the number of each node like may be changed variously depending on the number of bio-signal data, type of physiological variables to be obtained, and the number of samplings.

Once the input data 211 and 212 are input to the blood pressure estimation model 220, the blood pressure estimation model 220 may perform sampling by extracting a predetermined number of samples from each channel of the input data 211 and 212 and may input values, obtained by sampling, to each node of the input layer 221. For example, assuming that there are four bio-signal data, each having a time length of 100, the processor 120 may configure a 100×4 multi-channel input data, and the blood pressure estimation model 220 may perform sampling by extracting, for example, 100 samples from each of the four channels, and then may input 400 values (e.g., amplitude), obtained by sampling, to each of 400 nodes of the input layer 221. The output layer 223 of the blood pressure estimation model 220 may process a result input through the hidden layers 222 to output the systolic blood pressure variation ΔSBP and/or the diastolic blood pressure variation ΔDBP. In this case, the blood pressure variation may include a difference or ratio between a blood pressure value at the calibration time and a blood pressure value at the blood pressure estimation time.

Figure 2E:
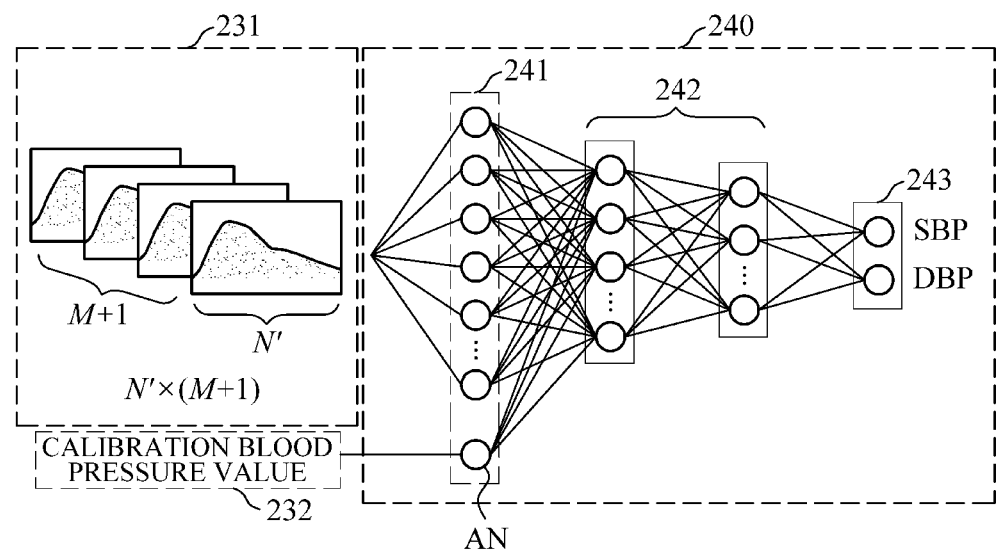

In some embodiments, as illustrated in FIG. 2E, a blood pressure estimation model 240 may be pretrained to output blood pressure values SBP and DBP at the current time, instead of the blood pressure variations. In addition to input data 231 configured based on the bio-signal data, the processor 120 may further input a calibration blood pressure value 232 to an additional node (ΔN) of an input layer 241 of the blood pressure estimation model 240. The input data 231 and the calibration blood pressure value 232, which are input to the input layer 241, may pass through hidden layers 242, to be output as blood pressure values SBP and DBP through the output layer 243. In this case, the processor 120 may further input additional data, such as user information, to another additional node of the input layer 241.

Figure 3:
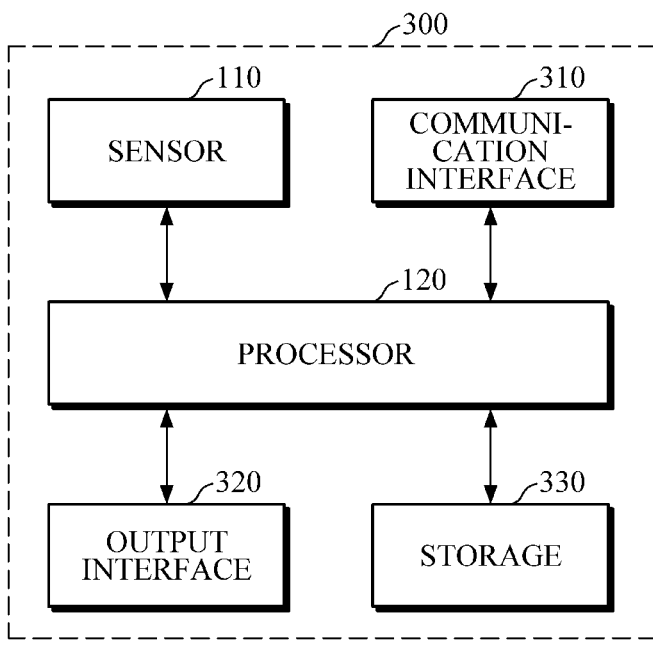
FIG. 3 is a block diagram illustrating an apparatus for estimating physiological variables according to another embodiment of the present disclosure.

FIG. 3 is a block diagram illustrating an apparatus for estimating physiological variables according to another embodiment of the present disclosure.

Referring to FIG. 3, an apparatus 300 for estimating physiological variables includes the sensor 110, the processor 120, a communication interface 310, an output interface 320, and a storage 330. The sensor 110 and the processor 120 are described in detail above, such that a description thereof will be omitted.

The communication interface 310 may be electrically connected to the processor 120 and may communicate with another electronic device under the control of the processor 120 to transmit and receive necessary data by using various communication techniques. In this case, the necessary data may include a reference physiological variable value, a physiological variable estimation model, a variation in physiological variables, a physiological variable estimation result, a bio-signal at a current time and a bio-signal at a calibration time which are measured by, for example, another electronic device. Another electronic device may include a blood pressure measuring device such as a cuff sphygmomanometer, a smartphone, a tablet PC, a desktop computer, a laptop computer, and/or a wearable device. However, the electronic device is not limited thereto. In this case, the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, and 5G communications. However, the communication techniques are not limited thereto.

The output interface 320 may output processing results of the sensor 110 and/or the processor 120 and may provide the results to a user. The output interface 320 may provide the user with information by various visual/non-visual methods using a visual output module such as a display, an audio output module such as a speaker, or a haptic module using vibrations, and/or tactile sensation. For example, the output interface 320 may output information, such as the physiological variable estimation result, warning and action based on the physiological variable estimation result.

The storage 330 may store various instructions related to operation of the respective components of the apparatus 100, data necessary for the sensor 110 and/or the processor 120 to estimate physiological variables, and/or the processing results of the sensor 110 and/or the processor 120. For example, the storage 330 may store a physiological variable estimation model, user information (e.g., gender, age, height, weight, health condition, etc.), raw data of a bio-signal generated at a physiological variable estimation time, preprocessed data obtained by preprocessing the raw data, features associated with physiological variables, multi-dimensional data, representative waveform data, a calibration physiological variable value, an estimated physiological variable value.

The storage 330 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, but is not limited thereto.

Figure 4A:
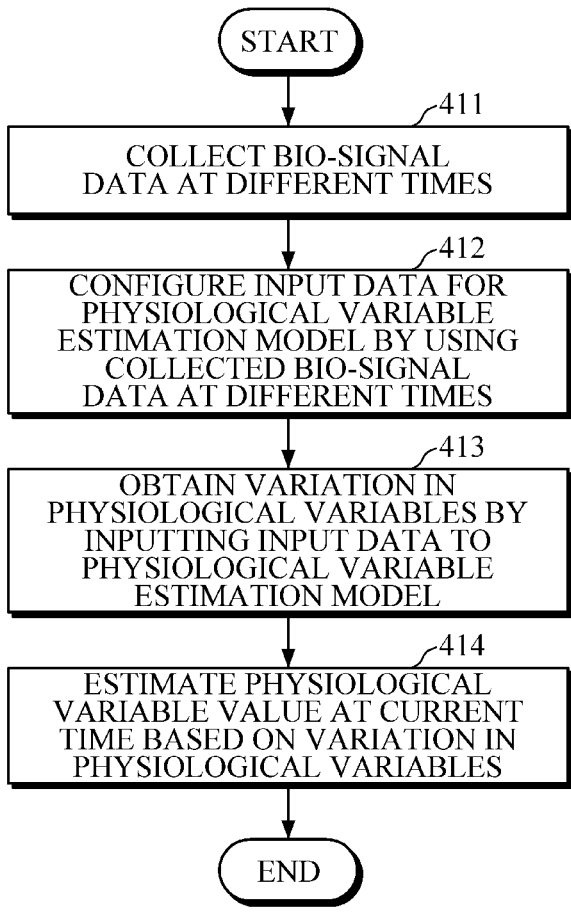
FIGS. 4A to 4C are flowcharts illustrating a method of estimating physiological variables according to embodiments of the present disclosure.

FIG. 4A is a flowchart illustrating a method of estimating physiological variables according to an embodiment of the present disclosure. FIG. 4A is an example of a method of estimating physiological variables performed by the apparatuses 100 and 300 for estimating physiological variables of FIGS. 1 and 3, which are described in detail above, and thus will be briefly described below.

First, the apparatus for estimating physiological variables may collect bio-signal data at different times in response to a request for estimating physiological variables in 411. For example, the apparatus for estimating physiological variables may measure a bio-signal at a current time from an object by using a sensor or may receive a bio-signal at the current time which is measured by another electronic device. In addition, the apparatus for estimating physiological variables may collect one or more bio-signal data at a previous calibration time from a memory, cloud, and/or another electronic device. In this case, the physiological variable data may include raw data of a bio-signal measured by the sensor, data obtained by preprocessing the raw data, representative waveform data extracted from the raw data or the preprocessed data, feature data associated with physiological variables and extracted from the raw data or the preprocessed data, or multi-dimensional data obtained by converting the raw data or the preprocessed data.

Then, the apparatus for estimating physiological variables may configure input data for a physiological variable estimation model based on the bio-signal data at different times in 412. The input data may be configured as multi-channel input data. In this case, if the bio-signal data differ in length, the apparatus for estimating physiological variables may adjust the data to be equal in length by adding a padding value to the data or by normalizing the data or cutting a partial section of the data.

Subsequently, the apparatus for estimating physiological variables may obtain a variation in physiological variables by inputting the input data to the physiological variable estimation model in 413. The physiological variable estimation model may be a model pretrained by machine learning, such as deep learning, to extract samples from each channel of the input data, to input the extracted sample values to an input node, and to output a variation in physiological variables through an output node.

Next, the apparatus for estimating physiological variables may estimate a physiological variable value at the current time based on the variation in physiological variables in 414. For example, the apparatus for estimating physiological variables may obtain the physiological variable value by linearly combining the obtained variation in physiological variables with a calibration physiological variable value.

Figure 4B:
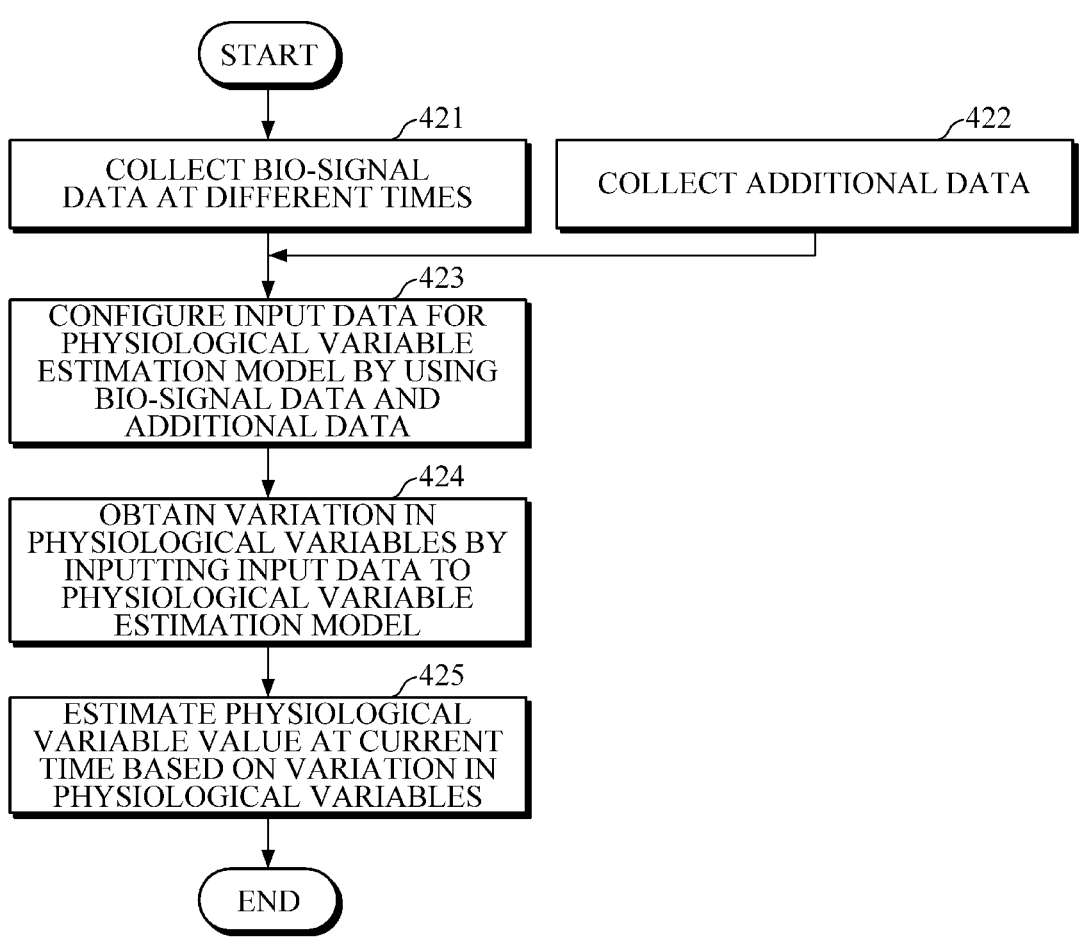

FIG. 4B is a flowchart illustrating a method of estimating physiological variables according to another embodiment of the present disclosure. FIG. 4B is an example of a method of estimating physiological variables performed by the apparatuses 100 and 300 for estimating physiological variables of FIGS. 1 and 3, which are described in detail above, and thus will be briefly described below.

First, the apparatus for estimating physiological variables may collect bio-signal data at different times in response to a request for estimating physiological variables in 421. The apparatus for estimating physiological variables may measure a bio-signal at a current time from an object by using a sensor or may receive a bio-signal at the current time which is measured by another electronic device, and may collect one or more bio-signal data at a previous calibration time from a memory.

Further, the apparatus for estimating physiological variables may collect additional data in addition to the bio-signal data in 422. The additional data may include a physiological variable value (e.g., blood pressure value) at a calibration time, user information (e.g., age, gender, weight, height, etc.), and/or values obtained by normalizing features associated with physiological variables. For example, the apparatus for estimating physiological variables may collect the physiological variable value at the calibration time and/or the user information from a memory, cloud, and/or another electronic device. In addition, the apparatus for estimating physiological variables may normalize a feature associated with blood pressure at the current time based on a feature associated with blood pressure at the calibration time.

Then, the apparatus for estimating physiological variables may configure input data for a physiological variable estimation model based on the bio-signal data and the additional data in 423. The input data may be configured as multi-channel data, and if the bio-signal data differ in length, the apparatus for estimating physiological variables may adjust the data to be equal in length by adding a padding value to the data or by normalizing the data or cutting a partial section of the data.

Subsequently, the apparatus for estimating physiological variables may obtain a variation in physiological variables by inputting the input data to the physiological variable estimation model in 424, and may estimate a physiological variable value at the current time based on the variation in physiological variables in 425.

Figure 4C:
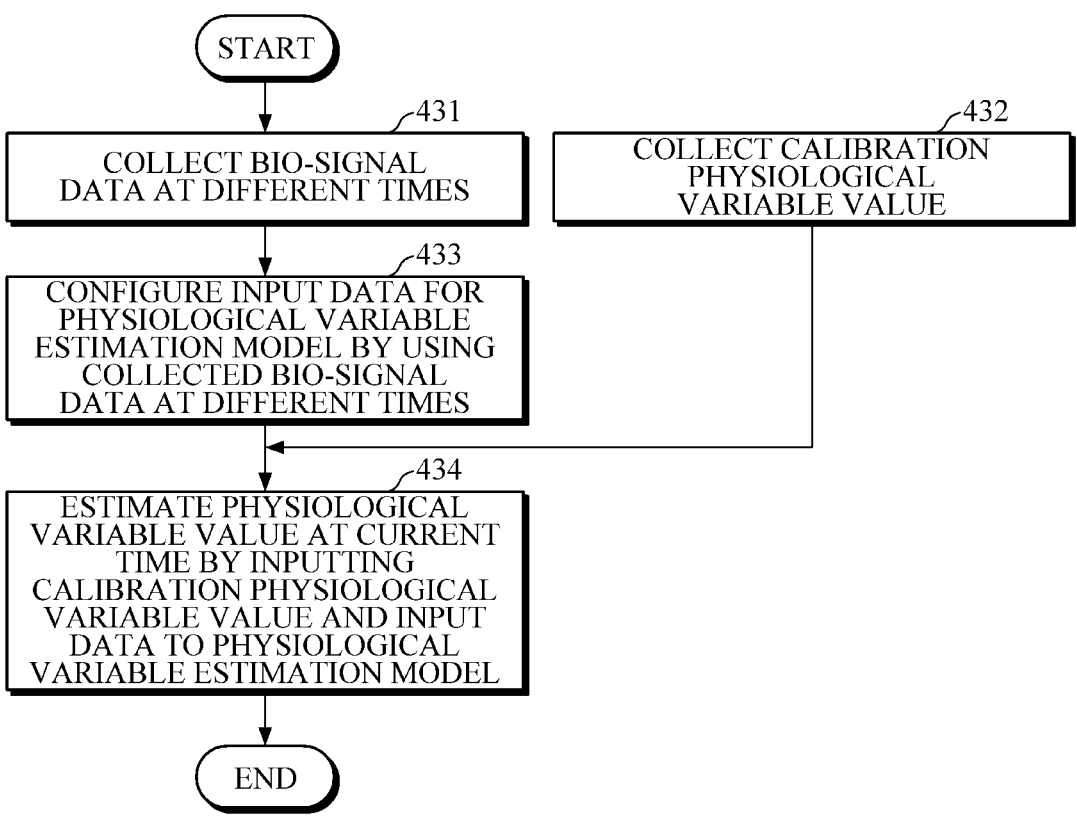

FIG. 4C is a flowchart illustrating a method of estimating physiological variables according to yet another embodiment of the present disclosure. FIG. 4C is an example of a method of estimating physiological variables performed by the apparatuses 100 and 300 for estimating physiological variables of FIGS. 1 and 3, which are described in detail above, and thus will be briefly described below.

First, the apparatus for estimating physiological variables may collect bio-signal data at different times in response to a request for estimating physiological variables in 431.

In addition, the apparatus for estimating physiological variables may collect a calibration physiological variable value in 432. The physiological variable value at the calibration time may be a blood pressure value measured by a device, for example, a cuff sphygmomanometer, from an object at the calibration time and may be received from a memory.

Then, the apparatus for estimating physiological variables may configure input data for a physiological variable estimation model based on the collected bio-signal data in 433. In this case, the apparatus for estimating physiological variables may configure the input data by further using additional data such as user information.

Subsequently, the apparatus for estimating physiological variables may estimate a physiological variable value at the current time by inputting the calibration physiological variable value and the input data to a physiological variable estimation model trained to output a physiological variable value at the current time in 434.

Figure 5:
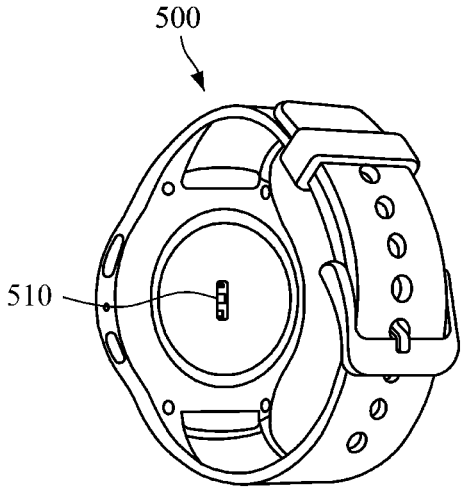
FIGS. 5 to 7 are diagrams illustrating examples of various structures of an electronic device including an apparatus for estimating physiological variables.
Figure 6:
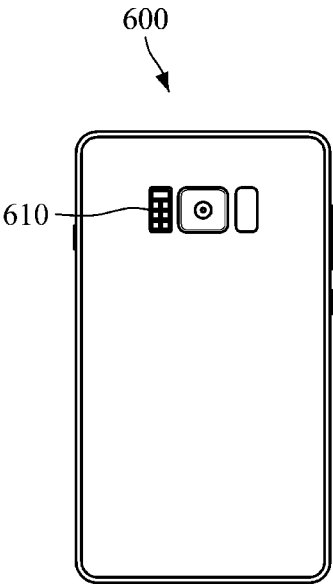
Figure 7:
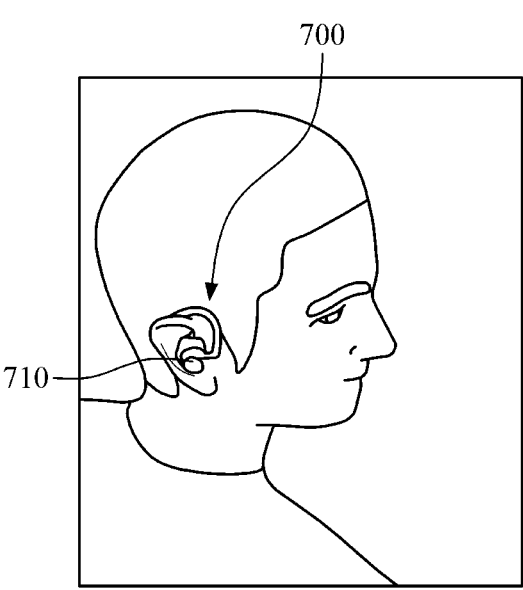

FIGS. 5 to 7 are diagrams illustrating examples of various structures of an electronic device including the apparatuses 100 and 300 for estimating physiological variables of FIG. 1 or FIG. 3.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, or home appliances or various Internet of Things (IoT) devices (e.g., home IoT device) based on Internet of Things (IoT) technology.

The electronic device may include a sensor device, a processor, an input device, a communication module, a camera module, an output device, a storage device, and a power module. All the components of the electronic device may be integrally mounted in a specific device or may be distributed in two or more devices. The sensor device may include the sensor of the apparatuses 100 and 300 for estimating physiological variables, and may further include an additional sensor, such as a gyro sensor, and/or a Global Positioning System (GPS).

The processor may execute programs, stored in the storage device, to control components connected to the processor, and may perform various data processing or computation, including estimation of bio-information. The processor may include a main processor, e.g., a central processing unit (CPU) or an application processor (AP), and an auxiliary processor, e.g., a graphics processing unit (GPU), an image signal processor (ISP), a sensor hub processor, or a communication processor (CP), which is operable independently from, or in conjunction with, the main processor.

The input device may receive a command and/or data to be used by each component of the electronic device, from a user. The input device may include, for example, a microphone, a mouse, a keyboard, or a digital pen (e.g., a stylus pen).

The communication module may support establishment of a direct (e.g., wired) communication channel and/or a wireless communication channel between the electronic device and other electronic device, a server, or the sensor device within a network environment, and performing of communication via the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, and/or a wired communication module, e.g., a local area network (LAN) communication module and/or a power line communication (PLC) module. These various types of communication modules may be integrated into a single chip, or may be separately implemented as multiple chips. The wireless communication module may identify and authenticate the electronic device in a communication network by using subscriber information (e.g., international mobile subscriber identity (IMSI)) stored in a subscriber identification module.

The camera module may capture still images or moving images. The camera module may include a lens assembly having one mor more lenses, image sensors, image signal processors, and/or flashes. The lens assembly included in the camera module may collect light emanating from a subject to be imaged.

The output device may visually/non-visually output data generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry (e.g., pressure sensor) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The haptic module may convert an electrical signal into a mechanical stimulus (e.g., vibration, motion) or electrical stimulus which may be recognized by a user by tactile sensation or kinesthetic sensation. The haptic module may include, for example, a motor, a piezoelectric element, and/or an electric stimulator.

The storage device may store operating conditions required for operating the sensor device, and various data necessary for other components of the electronic device. The various data may include, for example, input data and/or output data for software and instructions associated with the software. The storage device may include a volatile memory and/or a non-volatile memory.

The power module may manage power supplied to the electronic device. The power module may be implemented as part of, for example, a power management integrated circuit (PMIC). The power module may include a battery, which may include a primary cell which is not rechargeable, a secondary cell which is rechargeable, and/or a fuel cell.

Referring to FIG. 5, the electronic device may be implemented as a wristwatch wearable device 500, and may include a main body and a wrist strap. A display is provided on a front surface of the main body, and may display various application screens, including an estimated physiological variable value, warning information, time information, received message information. A sensor device 510 may be disposed on a rear surface of the main body.

Referring to FIG. 6, the electronic device may be implemented as a mobile device 600 such as a smartphone. The mobile device 600 may include a housing and a display panel. The housing may form an exterior of the mobile device 600. The housing has a first surface, on which a display panel and a cover glass may be disposed sequentially, and the display panel may be exposed to the outside through the cover glass. A sensor device 610, a camera module and/or an infrared sensor may be disposed on a second surface of the housing. The processor and various other components may be disposed in the housing.

Referring to FIG. 7, the electronic device may be implemented as an ear-wearable device 700. The ear-wearable device 700 may include a main body and an ear strap. A user may wear the ear-wearable device 700 by hanging the ear strap on the auricle. The ear strap may be omitted depending on a shape of the ear-wearable device 700. The main body may be inserted into the external auditory meatus. A sensor device 710 may be mounted in the main body. Further, the processor may be disposed in the main body, and may estimate physiological variables by using a PPG signal measured by the sensor device 710. Alternatively, the ear-wearable device 700 may estimate physiological variables by interworking with an external device. For example, the ear-wearable device 700 may transmit the PPG signal, measured by the sensor device 710 of the ear-wearable device 700, to an external device, e.g., a smartphone, a tablet PC, through a communication module provided in the main body, so that a processor of the external device may estimate physiological variables, and may output the estimated physiological variable value through a sound output module provided in the main body of the ear-wearable device 700.

In some embodiments, the above method can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing example embodiments can be readily deduced by programmers of ordinary skill in the art to which the disclosure pertains.

The present disclosure has been described herein with regard to example embodiments. However, it will be obvious to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. An apparatus for estimating blood pressure, the apparatus comprising:
   a sensor configured to measure a bio-signal a plurality of times from an object;
   a memory configured to store the measured bio-signals;
   a processor comprising a neural network-based blood pressure estimation model configured to:
      collect the bio-signal measured at a current time and additional bio-signals measured at least one or more times at a calibration time from the memory, as input data,
      input the input data into the neural network-based blood pressure estimation model to obtain a blood pressure variation over a time period from the calibration time to the current time, and
      estimate blood pressure by combining the obtained blood pressure variation and a blood pressure at the calibration time, and
   a display configured to display the estimated blood pressure and warning information based on the estimated blood pressure,
   wherein the processor is configured to adjust each of the bio-signals to be equal in length by normalizing the bio-signals by (i) adding a predetermined padding value to each of the bio-signals having a shorter length in comparison to a predetermined length, and (ii) cutting a predetermined region of bio-signals having a longer length in comparison to the predetermined length,
   wherein the blood pressure variation includes at least one of a difference and a ratio between the blood pressure at the calibration time and a blood pressure at the current time.

2. The apparatus of claim 1, wherein the bio-signal comprises at least one of photoplethysmogram (PPG), Electrocardiography (ECG), Electromyography (EMG), impedance plethysmogram (IPG), Pressure wave, video plethysmogram (VPG), Speckle-plethysmogram (SPG), Magnetic-plethysmograph (MPG), Ballistocardiogram (BCG), or Seismocardiogram (SCG).

3. The apparatus of claim 1, wherein the processor is further configured to collect user information as the input data.

* * * * *